United States Patent [19]

Lunkenheimer

[11] Patent Number: 4,904,811
[45] Date of Patent: Feb. 27, 1990

[54] (Z)-2-CYANO-2-OXIMINO-ACETYL CHLORIDES

[75] Inventor: Winfried Lunkenheimer, Wuppertal, Fed. Rep. of Germany

[73] Assignee: Bayer Aktiengesellschaft, Leverkusen, Fed. Rep. of Germany

[21] Appl. No.: 72,087

[22] Filed: Jul. 10, 1987

[30] Foreign Application Priority Data

Jul. 28, 1986 [DE] Fed. Rep. of Germany ....... 3625434

[51] Int. Cl.$^4$ .......................................... C07C 121/84
[52] U.S. Cl. .................................. 558/301; 548/207; 548/262; 548/378
[58] Field of Search ....................... 548/207, 262, 378; 558/301

[56] References Cited

U.S. PATENT DOCUMENTS 4,782,086 11/1988 Lunkenheimer et al. .......... 514/521

FOREIGN PATENT DOCUMENTS 0201999 11/1986 European Pat. Off. .
0206004 12/1986 European Pat. Off. .
3035145 4/1981 Fed. Rep. of Germany ...... 558/301
3322010 12/1984 Fed. Rep. of Germany ...... 558/301
646143 11/1984 Switzerland .
1389195 4/1975 United Kingdom .
1399088 6/1975 United Kingdom .

OTHER PUBLICATIONS

Kay, et al., Chemical Abstracts, vol. 106: 213424k (1987) Abstract of GB 2,173,791, 10/22/86.

Primary Examiner—Mukund J. Shah
Assistant Examiner—Diana G. Rivers
Attorney, Agent, or Firm—Sprung Horn Kramer & Woods

[57] ABSTRACT

A Z compound, substantially free of the E-isomers, of the formula

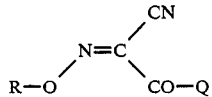

in which
Q represents Cl or OM,
M represents hydrogen or an alkali metal atom,
R represents optionally substituted cycloalkyl or the

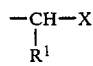

group,
R$^1$ represents hydrogen or alkyl, and
X represents hydrogen, alkyl, alkenyl, alkinyl, cyano, optionally substituted cycloalkyl, optionally substituted aryl, or an optionally substituted heterocyclic ring which is optionally fused to a benzene ring.

The compounds wherein Q is Cl are produced by reacting the compounds wherein Q is—OM with a chlorinating agent. The products are intermediates for fungicides.

4 Claims, No Drawings

(Z)-2-CYANO-2-OXIMINO-ACETYL CHLORIDES

The present invention relates to new Z isomers of N-(2-cyano-2-oximino)-acetyl chloride, a process for their preparation and their use as intermediates for the synthesis of mixtures of E/Z isomers and pure Z isomers of 2-cyano-2-oximino-acetamides, which can be employed as plant-protecting agents, particularly as fungicides.

The new (Z)-2-cyano-2-oximino-acetyl chlorides are defined by the general formula (I)

$$\begin{array}{c} \text{CN} \\ \text{N=C} \\ \text{R—O} \quad \text{CO—Cl} \end{array} \quad (I)$$

in which R represents optionally substituted cycloalkyl or the $$\begin{array}{c} -\text{CH}-\text{X} \\ | \\ \text{R}^1 \end{array}$$

group, where
R$^1$ represents hydrogen or alkyl, and
X represents hydrogen, alkyl, alkenyl, alkinyl, cyano, optionally substituted cycloalkyl, optionally substituted aryl, or an optionally substituted heterocyclic ring which is optionally fused to a benzene ring.

It has furthermore been found that the new (Z)-2-cyano-2-oximino-acetyl chlorides of the general formula (I) are obtained when compounds of the general formula (II)

$$\begin{array}{c} \text{CN} \\ \text{N=C} \\ \text{R—O} \quad \text{CO—OM} \end{array} \quad (II)$$

in which
R has the abovementioned meaning, and
M represents hydrogen or an alkali metal atom, such as, for example, sodium or potassium,
are reacted with a halogenating agent, if appropriate in the presence of a diluent and if appropriate in the presence of a catalyst.

The new (Z)-2-cyano-2-oximino-acetyl chlorides are important intermediates for the preparation of plant-protecting active compounds. Thus, the substances of the general formula (I) are suitable, for example, as starting materials for the synthesis of mixtures of E/Z isomers and the pure Z isomers and E isomers of N$^\alpha$-(2-cyano-2-alkoximinoacetyl)-amino acid derivatives and -peptides, which all have very good fungicidal activity.

Surprisingly, the mixtures of E/Z isomers and the pure Z isomers and E isomers of N$^\alpha$-(2-cyano-2-alkoximinoacetyl)-amino acid derivatives and -peptides, which can be prepared from the (Z)-2-cyano-2-oximino-acetyl chlorides of the general formula (I) according to the invention by reaction with the appropriate amines in the presence of an acid-binding agent, are superior, with respect to their fungicidal activity, to the compound zinc ethylene-1,2-bisdithiocarbamate, which is known from the state of the art.

The general formula I provides a general definition of the substances according to the invention. Preferred compounds of the general formula (I) are those in which R represents cycloalkyl, having 3 to 6 carbon atoms, which is optionally mono- to trisubstituted by halogen or methyl, the substituents being identical or different, or the $$\begin{array}{c} -\text{CH}-\text{X} \\ | \\ \text{R}^1 \end{array}$$

group, where
R$^1$ represents hydrogen or methyl, and
X represents hydrogen, straight-chain or branched alkyl having 1 to 8 carbon atoms, vinyl, ethinyl, cyano, cyclopropyl which is optionally mono- or disubstituted by halogen, the substituents being identical or different, phenyl which is optionally substituted by halogen or alkyl having 1 to 4 carbon atoms, or an optionally substituted heterocyclic ring which is optionally fused to a benzene ring, contains 1 to 3 identical or different hetero atoms from the group comprising nitrogen, oxygen and sulphur, and may be substituted by halogen or alkyl having 1 to 4 carbon atoms. Particularly preferred compounds of the general formula (I) are those in which R represents cyclopentyl or cyclohexyl which are optionally mono- or disubstituted, by chlorine or methyl, the substituents being identical or different, or represents the $$\begin{array}{c} -\text{CH}-\text{X} \\ | \\ \text{R}^1 \end{array}$$

group,
where
R$^1$ represents hydrogen or methyl, and
X represents hydrogen, methyl, ethyl, vinyl, ethinyl, cyano, cyclopropyl which is optionally mono- or disubstituted by chlorine, represents phenyl which is optionally substituted by chlorine, methyl or ethyl, represents pyrazol-1-yl or 1,2,4-triazol-1-yl, each of which is optionally substituted by chlorine or methyl, or represents the $$\begin{array}{c} \text{(benzene ring with } =\text{N—SO}_2 \text{ substituent)} \end{array}$$

radical.

If, for example, potassium (Z)-2-cyano-2-methoximino-acetate is used as starting material and oxalyl chloride is used as halogenating agent, the course of the reaction of the process according to the invention may be represented by the following equation:

$$\begin{array}{c} \text{CN} \\ \text{N=C} \\ \text{CH}_3\text{—O} \quad \text{CO—OK} \end{array} \xrightarrow{\text{ClOC—COCl}}$$

$$\begin{array}{c} \text{CN} \\ \text{N=C} \\ \text{CH}_3\text{—O} \quad \text{CO—Cl} \end{array}$$

The general formula (II) provides a general definition of the compounds which are required as starting materials for carrying out the process according to the invention. In this formula, R preferably represents those meanings which have already been mentioned for the radical R in connection with the description of the substances of the general formula (I) according to the invention. M preferably represents hydrogen, potassium or sodium, particularly sodium or potassium.

The compounds of the general formula (II) were hitherto not known. However, they can be prepared in a simple fashion by processes which are known in principle. Thus, for example, the compounds of the general formula (II) are obtained by saponifying the carboxylic acid esters of the general formula (III)

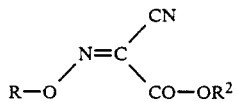

in which
R has the abovementioned meaning, and
$R^2$ represents methyl or ethyl,
with an alkali metal hydroxide, such as, for example, potassium or sodium hydroxide, in a solvent, such as, for example, water, methanol or ethanol, or by initially reacting the carboxylic acid esters with an alkali metal hydroxide, such as, for example, sodium hydroxide, and subsequently with an acid, such as, for example, hydrochloric acid or sulphuric acid, or with an acidic ion exchanger, in the presence of a diluent, such as, for example, water, alcohols, ethers or mixtures of alcohols or ethers with water, at temperatures between 0 and 80° C., preferably between 20 and 40° C.

Some of the carboxylic acid esters of the general formula (III) are known (cf., for example, J. Antibiot. 37, 557 (1984)).

They can be obtained by dehydrating amides of the general formula (IV)

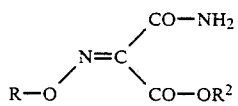

in which R and $R^2$ have the abovementioned meaning, using a dehydrating agent, such as, for example, trifluoroacetic anhydride, trichloroacetyl chloride, mesyl chloride, tosyl chloride, titanium tetrachloride or N,N-dimethylchloroformimidium chloride, in the presence of a tertiary base, such as, for example, pyridine, triethylamine or N-methylmorpholine, and if appropriate in the presence of a solvent, such as, for example, dioxane, tetrahydrofuran, acetonitrile, methylene chloride or pyridine, at temperatures between −20 and 60° C.

Some of the amides of the general formula (IV) are known (cf., for example, J. Antibiot, 37, 557 (1984)).

They can be obtained by reacting compounds of the general formula (V)

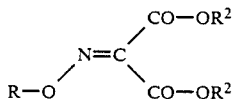

in which R and $R^2$ have the abovementioned meanings, with ammonia in the presence of a solvent, such as, for example, methanol, ethanol, diethyl ether, dimethoxyethane, dimethylformamide or acetonitrile at temperatures between −20° C. and 30° C.

Some of the compounds of the general formula (V) are known (cf., for example, J. Antibiot. 37, 557 (1984)).

They can be obtained by reacting compounds of the general formula (VI)

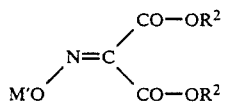

in which
$R^2$ has the abovementioned meaning, and
M′ represents hydrogen or an alkali metal atom, such as, for example, sodium or potassium,
with compounds of the general formula (VII)

R-W                                                    (VII)

in which
R has the abovementioned meaning, and
W represents halogen or a sulphonyloxy radical, such as, preferably, chlorine, bromine, iodine, —OSO$_2$OCH$_3$, —OSO$_2$OC$_2$H$_5$, —OSO$_2$CH$_3$ or

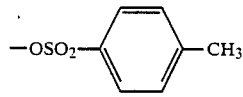

if appropriate in the presence of a base, such as, for example, potassium carbonate, triethylamine or diazabicycloundecane (DBU), and in the presence of a solvent, such as, for example, acetone, dimethylformamide, dimethyl sulphoxide or acetonitrile, at temperatures between 0 and 120° C.

The compounds of the general formulae (VI) and (VII) are generally known compounds of organic chemistry.

Suitable diluents for the process according to the invention are inert organic solvents. These preferably include ethers, such as diethyl ether; chlorinated hydrocarbons, such as methylene chloride, esters, such as ethyl acetate; nitriles, such as acetonitrile; and hydrocarbons, such as toluene.

The process according to the invention is carried out using a halogenating agent. All halogenating agents which can conventionally be used can be employed. Oxalyl chloride, phosphorus pentachloride, thionyl chloride or phosgene are preferably used. It should be ensured here that the halogenating agent does not contain any free hydrogen chloride, since isomerization to the E isomer can otherwise occur during the process.

The process according to the invention is, if appropriate, carried out in the presence of a catalyst. These preferably include dimethylformamide and triphenyl phosphine.

The reaction temperatures may be varied within a relatively wide range when carrying out the process according to the invention. In general, the process is carried out at temperatures between −20° C. and 80° C., preferably at temperatures between −10° C. and 30° C., particularly at 0° C.

When carrying out the process according to the invention, 1 to 10 moles, preferably 1 to 3 moles, of halogenating agent are generally employed per mole of the compound of the general formula (II). In order to isolate the compound of the general formula (I) the reaction mixture is worked up in a conventional fashion.

The (Z)-2-cyano-2-oximino-acetyl chlorides of the general formula (I) according to the invention are suitable as intermediates for the synthesis of mixtures of E/Z isomers and the pure Z and E isomers of 2-cyano-2-oximino-acetamides, which can be used as plant-protecting agents, preferably as fungicides.

Thus, for example, 2-cyano-2-oximino-acetamides of the general formula (VIII)

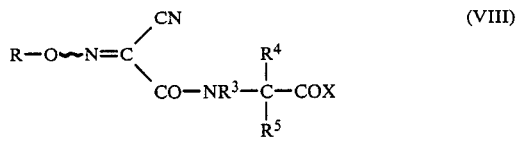

in which
R represents alkyl,
$R^3$ represents hydrogen, alkyl, optionally substituted phenyl or optionally substituted benzyl;
$R^4$ represents hydrogen or alkyl;
$R^5$ represents hydrogen, alkyl, alkoxycarbonylalkyl, hydroxycarbonylalkyl, aminocarbonylalkyl, azolylalkyl, cyanoalkyl, hydroxyalkyl, alkenyl, alkinyl, optionally substituted cycloalkyl, optionally substituted phenyl or phenylalkyl, and the $R^6$—$SO_n$—Z group,
where
$R^6$ represents hydrogen, alkyl or optionally substituted phenylalkyl;
n represents the numbers 0, 1 or 2, and
Z represents a straight-chain or branched alkylene chain;
$R^3$ and $R^5$, together with the nitrogen atom and the carbon atom to which they are bound, represent a 5- or 6-membered heterocyclic ring;
$R^4$ and $R^5$, together with the carbon atom to which they are bound, represent cycloalkylidene, and
X represents the —$OR^I$ or $NR^{II}R^{III}$ group,
where
$R^I$ represents hydrogen, alkyl, alkenyl or alkinyl;
$R^{II}$ represents hydrogen or alkyl;
$R^{III}$ represents hydrogen, alkyl, alkenyl, alkinyl, halogenoalkyl, alkoxyalkyl, dialkylaminoalkyl, alkoxycarbonylalkyl, hydroxycarbonylalkyl, aminocarbonylalkyl, alkylaminocarbonylalkyl, dialkylaminocarbonylalkyl, cyanoalkyl, optionally substituted phenylalkyl, optionally substituted phenyl or optionally substituted cycloalkyl, or $R^{II}$ and $R^{III}$, together with the nitrogen atom to which they are bound, represent an optionally substituted heterocyclic ring which may contain further hetero atoms, can be prepared by reacting the (Z)-2-cyano-2-oximinoacetyl chlorides of the genereal formula (I)

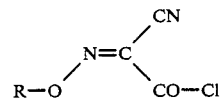

in which R represents alkyl with amino acid derivatives of the general formula (IX)

in which $R^3$, $R^4$, $R^5$ and X have the abovementioned meanings, if appropriate in the presence of a catalyst, if appropriate in the presence of an acid-binding agent and if appropriate in the presence of a diluent.

Suitable diluents for the reaction of the (Z)-2-cyano-2-oximino-acetyl chlorides of the general formula (I) according to the invention with amino acid derivatives of the general formula (IX) are inert organic solvents. These include ketones, such as acetone or ethyl methyl ketone; esters, such as ethyl or methyl acetate; amides, such as dimethylformamide; nitriles, such as acetonitrile; chlorinated hydrocarbons, such as methylene chloride or chloroform, hydrocarbons, such as toluene; or ethers, such as tetrahydrofuran; or mixtures thereof.

Suitable acid-binding agents for the reaction of the (Z)-2-cyano-2-oximino-acetyl chlorides of the general formula (I) according to the invention with amino acid derivatives of the general formula (IX) are conventional inorganic or organic acid acceptors. These preferably include tertiary amines, such as triethylamine, pyridine or N-methylmorpholine; and inorganic bases, such as sodium carbonate or calcium carbonate.

The reaction of the (Z)-2-cyano-2-oximino-acetyl chlorides of the general formula (I) according to the invention with amino acid derivatives of the general formula (IX) is, if appropriate, carried out in the presence of a catalyst. Examples which may be mentioned are 4-dimethylaminopyridine, 1-hydroxybenzotriazole or dimethylformamide.

The temperatures may be varied within a relatively wide range during the reaction of the (Z)-2-cyano-2-oximino-acetyl chlorides of the general formula (I) according to the invention with amino acid derivatives of the general formula (IX). In general, the reaction is carried out between −60 to +120° C., preferably at −20 to +40° C.

The compounds of the general formula (VIII) are produced, depending on the reaction conditions, as mixtures of E/Z isomers or as pure Z isomers. The E/Z isomerization here if favored by the presence of free hydrochloric acid.

The reaction of the (Z)-2-cyano-2-oximino-acetyl chlorides of the general formula (I) according to the invention with amino acid derivatives of the general formula (IX) is preferably carried out using equimolar amounts, a subequimolar or superequimolar amount of the base being employed, depending on the desired reaction product (mixture of E/Z isomers or pure Z isomer).

The mixtures of E/Z isomers and pure Z isomers of $N^\alpha$-(2-cyano-2-alkoximinoacetyl)-amino acid derivatives of the general formula (VIII) which can be prepared from the compounds of the general formula (I) according to the invention have very good fungicidal properties.

PREPARATION EXAMPLES
EXAMPLE 1

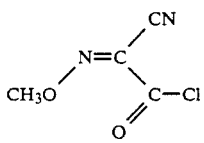

23.5 g (0.14 mol) of well-dried potassium (Z)-2-cyano-2-methoximino-acetate are suspended in 350 ml of absolute ether, a few drops of absolute dimethylformamide are added, 53.4 g (0.42 mol) of oxalyl chloride (previously stirred with 2 g of potassium carbonate for 1 hour) are added dropwise at 0° C. over 35 minutes, and the mixture is stirred for 2 hours at 0° C. The reaction mixture is filtered, the filtrate is evaporated in vacuo, and the residue is evaporated twice with dry dichloromethane in vacuo. 15.7 g (76% of theory) of (Z)-2-cyano-2-methoximino-acetyl chloride are obtained as an orange oil which is immediately reacted further.

PREPARATION OF THE STARTING MATERIAL:

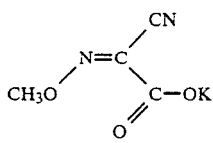

A solution of 11.8 g (0.21 mol) of potassium hydroxide in 80 ml of water is added dropwise to a solution of 34.3 g (0.2 mol) of ethyl (Z)-2-cyano-2-methoximino-acetate (91 percent strength) in 200 ml of ethanol, and the mixture is stirred for a further 1.5 hours at 40° C. The reaction solution is evaporated in vacuo at 40° C., and the residue is washed with ethanol and ether and dried in vacuo at room temperature.

28.3 g (85% of theory) of potassium (Z)-2-cyano-2-methoximino-acetate are obtained as a beige powder which decomposes explosively at 111° C. (peak temperature of differential thermoanalysis).

The Z configuration is confirmed by $^{13}$C NMR.

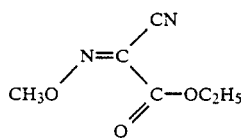

71.4 g (0.336 mol) of trifluoroacetic anhydride (99 percent strength) are added dropwise at 0° C. over 25 minutes to a solution of 33.5 g (0.177 mol) of 92 percent strength (Z)-2-methoximino-malonic acid monoamide ethyl ester and 28.0 g (0.35 mol) of pyridine in 260 ml of dry dioxane, and the mixture is stirred for 2 hours at room temperature. The reaction mixture is diluted using 260 ml of dichloromethane, washed twice with 200 ml of water in each case, with 150 ml of 10 percent strength sodium bicarbonate solution and with 200 ml of water, dried over sodium sulphate and evaporated in vacuo.

23.4 g (74% of theory) of ethyl (Z)-2-cyano-2-methoximinoacetate are obtained, in a purity of 88% (GC), as a red-brown oil of refractive index $n^{20}_D = 1.4399$.

The Z configuration is confirmed by $^{13}$C NMR.

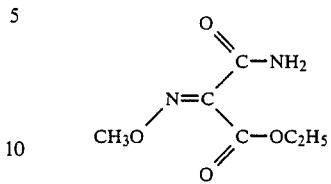

115 ml (0.587 mol) of a 5.1 M solution of ammonia in methanol are added dropwise to a solution of 44.2 g (0.196 mol) of 90 percent strength diethyl 2-methoximinomalonate in 200 ml of absolute ethanol, and the mixture is stirred for 24 hours at room temperature.

After evaporation in vacuo, 36.8 g (99% of theory) of (Z)-2-methoximino-malonic acid monoamide ethyl ester remain, in a purity of 92% according to gas chromatography), as a yellow-brown oil of refractive index $n^{20}_D = 1.4716$.

The Z configuration was confirmed by $^{13}$C NMR.

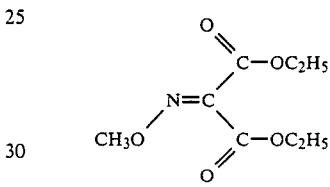

138 g (1 mol) of potassium carbonate are added to a solution of 108.9 g (0.5 mol) of 87 percent strength diethyl 2-hydroximino-malonate in 400 ml of dimethyl sulphoxide, 81.2 g (0.625 mol) of dimethyl sulphate are added dropwise over 20 minutes, the temperature increasing to 70° C., and the mixture is stirred for 3 hours at 60° C. After cooling, the mixture is filtered, and the filtrate is poured into 1 l of water and extracted three times with 600 ml of toluene/ethyl acetate (5:1) in each case. The extract, washed with 600 ml of water, is dried over sodium sulphate and evaporated in vacuo.

73.9 g (69% of theory) of diethyl 2-methoximinomalonate are thus obtained, in a purity of 95% (according to gas chromatography), as an orange oil having a refractive index $n^{20}_D = 1.4400$.

PREPARATION OF A SUBSEQUENT PRODUCT

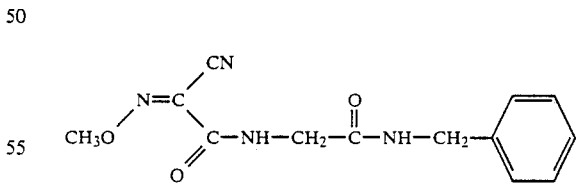

Z isomer 12.2 g (0.12 mol) of triethylamine are added to a solution of 12.3 g (0.05 mol) of glycine benzylamide hydrobromide in 100 ml of dry dimethylformamide, and 7.4 g (0.05 mol) of (Z)-2-cyano-2-methoximino-acetyl chloride are added dropwise at 0° C., and the reaction mixture is stirred for 1 hour at 0° C. and 17 hours at room temperature. The solvent is removed by distillation in vacuo, the residue is dissolved in 250 ml of dichloromethane, and the solution is washed with 100 ml of 1M hydrochloric acid, 100 ml of saturated sodium bicarbonate solution and 150 ml of water, dried over sodium sulphate and evaporated in vacuo. The residue is recrystallized from toluene/ethyl acetate/ligroin (1:1:1).

7.35 g (53.6% of theory) of $N^\alpha$-[(Z)-2-cyano-2-methoximino-acetyl]-glycine benzylamide of melting point 120–121° C. are obtained.

It is understood that the specification and examples are illustrative but not limitative of the present invention and that other embodiments within the spirit and scope of the invention will suggest themselves to those skilled in the art.

I claim:

1. A Z compound, substantially free of the E-isomers, of the formula

in which

Q represents Cl or OM,

M represents hydrogen or an alkali metal atom,

R represents cycloalkyl, having 3 to 6 carbon atoms, the

group, $R^1$ represents hydrogen or methyl, and

X represents hydrogen, straight-chain or branched alkyl having 1 to 8 carbon atoms, vinyl, ethinyl, cyano, cyclopropyl or phenyl.

2. A Z compound, substantially free of the E-isomers according to claim 1, in which Q represents Cl.

3. A compound according to claim 2, in which R represents the

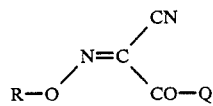

group, $R^1$ represents hydrogen or methyl, and

X represents hydrogen, methyl or ethyl.

4. A Z-compound, substantially free of the E-isomer, according to claim 2, in which R represents methyl.

* * * * *